United States Patent [19]

Schwan et al.

[11] 4,160,093
[45] Jul. 3, 1979

[54] 6-ETHYL-6,9-DIHYDRO-9-OXOPYRAZOLO[3,4-f]QUINOLINE-9-CARBOXYLIC ACID

[75] Inventors: Thomas J. Schwan; Raymond Freedman, both of Norwich, N.Y.

[73] Assignee: Morton-Norwich Products, Inc., Norwich, N.Y.

[21] Appl. No.: 899,372

[22] Filed: Apr. 24, 1978

[51] Int. Cl.² .................................... C07D 471/04
[52] U.S. Cl. .................................... 546/82; 424/258
[58] Field of Search ................ 260/287 CF; 546/82

[56] References Cited

U.S. PATENT DOCUMENTS 3,313,817  4/1967  Lesher ..................... 260/287 CF
3,714,170  1/1973  Dohmori et al. .......... 260/287 CF

OTHER PUBLICATIONS

Elderfield, Heterocyclic Compounds, (1952), p. 38.

Primary Examiner—Donald G. Daus
Assistant Examiner—David E. Wheeler
Attorney, Agent, or Firm—Anthony J. Franze

[57] ABSTRACT

6-Ethyl-6,9-dihydro-9-oxopyrazolo[3,4-f]quinoline-8-carboxylic acid of the formula:

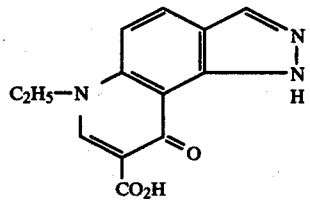

is useful as an antibacterial agent.

1 Claim, No Drawings

6-ETHYL-6,9-DIHYDRO-9-OXOPYRAZOLO[3,4-F]QUINOLINE-9-CARBOXYLIC ACID

This invention relates to the compound 6-ethyl-6,9-dihydro-9-oxopyrazolo[3,4-f]quinoline-8-carboxylic acid which was reported in 1977 (J. Heterocycl. Chem. 14,1175 (1977)). It possesses a broad spectrum of antibacterial activity and is thus adapted to be combined in various forms such as dusts, sprays, suspensions, unguents, and the like using commonly employed excipients to provide compositions capable of inhibiting and eradicating susceptable bacterial species. The gamut of its antibacterial potency as determined using the commonly employed broth dilution technique is illustrated here below:

| Organism | Minimum inhibiting concentration in mcg/ml |
| --- | --- |
| Shigella flexneri | 12.500 |
| Proteus mirabilis | 25.000 |
| Escherichera coli | 12.500 |
| Serratia marcescens | 12.500 |
| Klebsiella pneumoniae | 12.500 |
| Enterobacter aerogenes | 12.500 |

In order that this invention may be readily available to those skilled in the art, the now preferred method for its preparation is included.

A. Ethyl 6,9-Dihydro-9-oxopyrazolo[3,4-f]quinoline-8-carboxylate

A mixture of 108 g (0.50 mole) of diethyl ethoxymethyl-enemalonate, 65.5 g (0.50 mole) of 6-aminoindazole and 500 ml Dowtherm A was stirred and heated at 235°–242° for 6.5 hrs. and the ethanol evolved was collected in a Dean-Stark apparatus (vol. collected: 55.0 ml; theoretical amount: 58.5 ml).

The mixture was allowed to cool to 80°, diluted with 1000 ml heptane, and stirred for 30 min. Filtration gave 99 g of the crude product.

Recrystallization from 2400 ml DMF gave, in two crops, 48.6 g (38%) of the product, m.p. 309°–311°.

Further recrystallization from DMF gave an analytical sample, m.p. 318°–320°.

Anal. Calc'd. for $C_{13}H_{11}N_3O_3$: C, 60.69; H, 4.31; N, 16.74. Found: C, 60.45; H, 4.47; N, 16.39.

B. Ethyl 6-Ethyl-6,9-dihydro-9-oxopyrazolo[3,4-f]quinoline-8-carboxylate

A mixture of 33.4 g (0.13 mole) of A, 17.94 g (0.13 mole) of $K_2CO_3$, and 20.28 g (0.13 mole) of iodoethane in 500 ml DMF was stirred at 57°–63° for 60 hrs., cooled to 25°, and poured into 2000 ml cold, stirred tap water. The solution was stirred for 20 min. and extracted with $2\times400$ ml $CHCl_3$. The combined extracts were dried ($MgSO_4$) and concentrated to dryness in vacuo to give 28.8 g of the crude product. The solid was boiled with alcohol and the suspension was refrigerated for 18 hrs. Filtration, washing with alcohol, air drying, and drying 60° gave 21.70 g (59%) of the product, m.p. 230°–234°.

An analytical sample, m.p. 231°–235°, was obtained by recrystallization from alcohol.

Anal. Calc'd. for $C_{15}H_{15}N_3O_3$: C, 63.15; H, 5.30; N, 14.73. Found: C, 63.03; H, 5.31; N, 14.63.

C. 6-Ethyl-6,9-dihydro-9-oxopyrazolo[3,4-f]quinoline-8-carboxylic Acid

A mixture of 11.40 g (0.04 mole) of B and 400 ml 10% KOH was stirred and refluxed for 4.0 hrs., filtered through glass wool while hot, and acidified to pH 5 with 6N HCl at 60°. The mixture was stirred at ambient temperature for 30 min. and the solid was filtered, washed with $2\times50$ ml $H_2O$, air dried, and dried at 60° for 18 hrs. to give 10.0 g (97%) of the product, m.p. 315°–318° (dec).

An analytical sample, m.p. 312°–315°, was obtained by recrystallization from DMF.

Anal. Calc'd for $C_{13}H_{11}N_3O_3$: C, 60.69; H, 4.31; N, 16.34. Found: C, 60.31; H, 4.24; N, 16.41.

What is claimed is:
1. The compound 6-ethyl-6,9-dihydro-9-oxopyrazolo[3,4-f]quinoline-8-carboxylic acid.

* * * * *